US006472433B2

(12) United States Patent
Wechter

(10) Patent No.: US 6,472,433 B2
(45) Date of Patent: Oct. 29, 2002

(54) METHOD FOR TREATMENT OF INFLAMMATION WITH R-NSAIDS

(75) Inventor: William J. Wechter, Ojai, CA (US)

(73) Assignee: Loma Linda University Medical Center, Loma Linda, CA (US)

( * ) Notice: Subject to any disclaimer, the term of this patent is extended or adjusted under 35 U.S.C. 154(b) by 0 days.

(21) Appl. No.: 09/797,022

(22) Filed: Mar. 1, 2001

(65) Prior Publication Data

US 2001/0012849 A1 Aug. 9, 2001

Related U.S. Application Data

(63) Continuation of application No. PCT/US99/20261, filed on Sep. 3, 1999.
(60) Provisional application No. 60/155,217, filed on Jul. 8, 1999.

(51) Int. Cl.[7] .................. A61K 31/19; A61K 31/42; A61K 31/40; A61K 31/38

(52) U.S. Cl. .................. 514/570; 514/375; 514/411; 514/413; 514/429; 514/448

(58) Field of Search ................. 514/570, 375, 514/411, 413, 429, 448

(56) References Cited

U.S. PATENT DOCUMENTS

| 5,200,198 A | 4/1993 | Geisslinger et al. |
| 5,206,029 A | 4/1993 | Brune et al. |
| 5,331,000 A | 7/1994 | Young et al. |
| 6,069,172 A | 5/2000 | Bertini et al. |

FOREIGN PATENT DOCUMENTS

| EP | 0 935 961 A2 | 1/1999 |
| WO | WO 94/28890 | 12/1994 |
| WO | WO 98/09603 | 3/1998 |

OTHER PUBLICATIONS

Schaible et al, Chemical Abstracts, vol. 129, abstract No. 197755, 1998.*
Buritova et al, Chemical Abstracts, vol. 129, abstract No. 326025, 1998.*
New Insights into the Site and Mode of Antinociceptive Action of Flurbiprofen Enantiomers, Gerd Geisslinger, Ph.D. and Hans–Georg Schaible, MD, *J Clin Pharmacol 1996: 36: 513–520.*
Pure Enantiomers of 2–Arylpropionic Acid: Tools in Pain Research and Improved Drugs in Rheumatology, Kay Brune, MD, Gerd Geisslinger, Ph.D. and S. Menzel–Soglowek, Ph.D—*J Clin Pharmacol 1992;32:944–952.*
Clinical Pharmacokinetics of Flurbiprofen and its Enantimomers, Neal M. Davies—*Drug Disposition; Clin Pharmacokinet 28 (2) 1995.*
Variability of Inversion of (R)—Flurbiprofen in Different Species, Sabine Menzel–Soglowek, Gerd Geisslinger, Winfried S. Beck, and Kay Brune—*Journal of Pharmaceutical Sciences* vol. 81, No. 9, Sep. 1992.
Disposition and Pharmacokinetics of R–flurbiprofen in Three Species: Demonstration of R– to S–Flurbiprofen Inversion in the Mouse, Rat and Monkey—William J. Wechter, E. David Murray, Jr. Karina M. Gibson, David D. Quiggle, and Douglas L. Leipold—*Laboratory of Chemical Endocrinology, Loma Linda University School of Medicine,* 1998.
Superaspirin, Jerome Groopman *The New Yorker*, Jun. 15, 1998 pp. 32–35.
Building a Better Aspirin, *Science*, vol. 280, May 22, 1998.
R–Flurbiprofen Chemoprevention and Treatment of Intestinal Adenomas in the APC Min/+ Mouse Model: Implications for Prophylazis and Treatment of Colon Caner, William Wechter, Darko Kantoci, E. David Murray, Jr. David D. Quiggle, Douglas D. Leipold, Karina M. Gibson, and John D. McCracker—*Cancer Research* 57, 4316–4324, Oct. 1, 1997.
Aspirin–like drugs may block pain idependently of prostaglandin synthesis inbibition, K. Brune, W.S. Beck, G. Geisslinger, S. Menzel–Soglowek, B.M. Peskar and B.A. Peskar—*Experientia 47 (1991).*
PIII–82 Effect of Flurbiprofen (FLU) Enantiomers on Prostaglandin E2 (POE2) and Substance P (SP) Levels in Human Suction Blister, G. Geisslinger, Ph.D., R. Oelkers, MD, W. Neupert, Ms. K.M. Williams, Ph.D., K. Brune, MD. Dept. of Exp & Clinical Pharmacology—*Clinical Pharmacology & Therapeutics* Feb. 1996.
XP–000874955 Pharmacoloical Differences Between the Optical Isomers if Ibufprofen: Evidence for Metabolic Inversion of the (–)–isomer, S.S. Adams, P.Bresloff, C.G. Mason, Research Department, The Boots Company Ltd., Nottingham, U.K.—*Communications, J.Pharm. Pharmac., 1976, 28,256.*

(List continued on next page.)

*Primary Examiner*—William R. A. Jarvis
(74) *Attorney, Agent, or Firm*—Knobbe Martens Olson & Bear LLP

(57) ABSTRACT

This invention relates to the use of enantiomerically pure R-NSAIDs for the treatment of inflammation. Preferably, the R-NSAID used is R-flurbiprofen and is administered in a dose of at least 5 milligrams per kilogram of body weight per day. The anti-inflammatory action of R-NSAIDs is due to their ability to interfere with the biosynthesis of COX-2 by inhibiting COX-2 mRNA synthesis, rather than by just blocking the action of the enzyme itself. In order to effect the inhibition of COX-2 mRNA synthesis, the R-NSAID must be present at relatively high doses. Because the R-NSAID is selective in its action, that is, it does not inhibit either COX-1 mRNA synthesis or the COX-1 enzyme itself, it can be administered in the required high doses because the tissue protective effects of prostaglandins made through the COX-1 pathway are not interfered with.

5 Claims, No Drawings

OTHER PUBLICATIONS

Differential Contribution of R and S Isomers in Ketoprofen Anti–inflammatory Activity: Role of Cytokine Modulation, Pietro Ghezzi, et al. —*The Journal of Pharmacology and Experimental Therapeutics* vol. 287, No. 8, 1998.

Stereoselective Cyclooxygenase Inhibition in Cellular Modeels by the Enantiomers of Ketoprofen, Nuria Suesa, et al.—*Chirality 5:589–595 (1993)*.

Pharmacokinetics of Enantiomers of Chrial Non–Steroidal Anti–Inflammatory Drugs, Fakhreddin Jamali—*European Journal of Drug Metabolism and Pharmacokinetics*, 1998, vol. 13, No. 1, pp 1–9.

The Effects of S– and R–flurbiprofen on the inflammation-evoked intraspinal release of immunoreactive substance P–a study with antibody microphobes, *Brain Research 798* (1998) 287–293; Hans–Georg Schaible, et al.

Peripheral and/or central effects of racemic–,S(+)– and R(–)–flurbiprofen on inflammatory nociceptive processes: a c–Fos protein study in the rat spinal cord; *British Journal of Phamacology* vol. 125(1), pp. 87–101; Jaroslava Buritova & Jean–Marie Besson, 1998.

* cited by examiner

METHOD FOR TREATMENT OF INFLAMMATION WITH R-NSAIDS

RELATED APPLICATION INFORMATION

This application is a continuation of PCT International Patent Application No. PCT/US99/20261, filed Sep. 3, 1999, and claims priority under 35 U.S.C. § 119(e) to U.S. application Ser. No. 09/146,395, filed Sep. 3, 1998, now abandoned, which was converted to Provisional Application Ser. No. 60/155,217 on Jul. 8, 1999.

FIELD OF THE INVENTION

The present invention relates to pharmaceutical compositions comprising enantiomerically pure R-NSAIDs and the methods of their use for the treatment of inflammation. Preferably, the R-NSAID used is R-flurbiprofen which is administered in a dose of at least 2.5 milligrams per kilogram of body weight per day.

BACKGROUND OF THE INVENTION

Nonsteriodal anti-inflammatory drugs (NSAIDs) have been in use for over a century beginning with aspirin. In recent decades the arylpropionic acid (APA) class of these drugs has gained wide acceptance.

Although the NSAIDs are known to be effective against pain and inflammation, there are often severe side effects and toxicity associated with chronic use of these drugs. Chronic NSAID use is known to cause gastric and duodenal ulceration, which may be severe enough to result in significant morbidity and mortality. Furthermore, NSAID use has been reported to be associated with renal and hepatic toxicities, increase in bleeding times due to disruption of platelet function, prolongation of gestation due to uterine effects, and a decreased white cell count in the blood. Because of the side effects and toxicity, many NSAIDs are no longer in use in human medicine as analgesics. Some of these include tiaprofenic acid, suprofen, carprofen, pirprofen, benoxaprofen, and indoprofen.

Some NSAIDs, including the APAs, exhibit molecular chirality and thus have R- and S-enantiomers. The APAs, with the exception of naproxen, are currently prescribed as racemates.

For a given NSAID, there can be a difference in the properties exhibited by the R- and S-enantiomers. One important difference relates to the activities of the two enantiomers in connection with prostaglandin synthesis.

Prostaglandins are autocoids, produced by the body, which serve a variety of functions. An important step in the biosynthesis of prostaglandins requires the use of two cyclooxygenase (COX) enzymes, COX-1 or COX-2. COX-1 is present throughout the body and makes the prostaglandins that, among other things, help keep the stomach lining intact and the aid proper function of the kidneys. COX-2 is made by the body only under certain conditions, such as in response to tissue injury, and the prostaglandins produced by it are associated with pain and inflammation.

Researchers found that the S-enantiomers of NSAIDs were much better at inhibiting prostaglandin synthesis than the R-enantiomer, having 15–100 or even 500 times higher prostaglandin synthetase inhibitory activities than the R-enantiomers in the rat. Yamaguchi et al., *Nippo Yakurigaku Zasshi*, 90:295–302 (1987). Thus, it was thought that the biological activity of NSAIDs resided principally if not only in the S-enantiomers. Some researchers went as far as to say that "at best, the R-isomers [of APAs] function as prodrugs for the therapeutically active S-forms" when the racemic drug is administered to the host, and that the R-enantiomers are "undesirable impurities in the active drug." Caldwell et al., *Biochem. Pharmacol.* 37:105–114 (1988).

Although the S-NSAIDs have the desired effect of inhibiting production of prostaglandins through the COX-2 pathway, they also inhibit the production through the COX-1 pathway and thus the bad side effects of NSAID use generally are also associated with the use of S-enantiomers.

Earlier studies by researchers in this field, as well as by the inventor himself, found that R-NSAIDs had little or no inhibiting effect on COX enzymes and prostaglandin production. What little anti-inflammatory effect existed was either found to be statistically insignificant or attributed to the S-enantiomer, the presence of which was due to either an enantiomerically impure dose of R-NSAID or inversion of the R-enantiomer in vivo. See K. Brune et al, Pure Enantiomers of 2-Arylpropionic Acids: Tools in Pain Research and Improved Drugs in Rheumatology, *J. Clin. Pharmacol.* 32:944–52, 946 (1992); K. Brune et al., Aspirin-like drugs may block pain independently of prostaglandin synthesis inhibition, *Experentia* 47:257–61, 260 (1991); U.S. Pat. No. 5,200,198 to Geisslinger et al.; and U.S. Pat. No. 5,206,029 to Brune et al.

Although the researchers did not find significant anti-inflammatory activity, there was evidence of other activity attributable to the R-enantiomer, such as amelioration of pain (see U.S. Pat. Nos. 5,200,198 and 5,206,029), treatment and prevention of cancer (see Wechter et al., R-Flurbiprofen Chemoprevention and Treatment of Intestinal Adenomas in the $APC^{min}$/+Mouse Model, Cancer Research 57:4316–24 (1997)), treatment of cystic fibrosis (see U.S. Pat. No. 5,981,592) and treating or delaying the onset of Alzheimer's Disease (see U.S. Pat. No. 6,160,018).

U.S. Pat. Nos. 5,200,198 and 5,206,029 disclose the use of mixtures of R- and S-flurbiprofen to treat diseases characterized by pain and/or inflammation. The inventors state that R-flurbiprofen has better pain amelioration activity than S-flurbiprofen, and that the known side effects are coupled with the anti-inflammatory effects in S-flurbiprofen. Thus, according to the inventions, if one were to create a medicament for the treatment of a disease that was characterized primarily by pain, one would use a mixture having an excess of the R-flurbiprofen, so as to maximize the effects against pain. The amount of S-flurbiprofen in the mixture would be minimized, so as to attain a balance between the needed anti-inflammatory activity and the undesired side effects which result from use of the S-enantiomer. If, according to the disclosures of the '198 and '029 patents, one wanted to create medicament for the treatment of a disease characterized by both pain and inflammation, one would increase the amount of S-flurbiprofen in the composition in order to have the needed anti-inflammatory effect and would have to accept the unwanted side effects.

A common test which is used to determine whether a compound has activity as an anti-inflammatory drug is the carrageenan paw test. In this test, the test compound is administered to several rats. Thereafter, a paw on each rat is injected with a solution of carrageenan in order to induce edema in the paw as a measure of inflammation. After three hours, the volume of the paw is measured using a plethysmometer. Reduction of edema by 30% or more, as compared to a control group which was not given the test compound, is considered indicative of anti-inflammatory activity.

In the '198 and '029 patents, there is described the results of the carrageenan paw test done using a dosage of 0.3 mg/kg of R- or S-flurbiprofen. The enantiomeric purity of the compounds used is not disclosed. For these tests, it was reported that the reduction of edema for the S-flurbiprofen was 64%, indicating anti-inflammatory activity, but for the R-flurbiprofen it was only 18% which does not indicate anti-inflammatory activity.

The inventors in the '198 and '029 patents, Brune and Geisslinger, later reported carrageenan paw tests using dosages of approximately 0.1 mg/kg, 0.3 mg/kg, 1 mg/kg, and 2.5 mg/kg of R- and S-flurbiprofen (*Experentia*, 47:257–261). Only at the highest dose, 2.5 mg/kg, did the R-flurbiprofen demonstrate a statistically significant reduction in inflammation. In a 1996 article entitled New Insights into the Site and Mode of Antinociceptive Action of Flurbiprofen Enantiomers (*J. Clin. Pharmcol.* 36:513–20), Brune and Geisslinger discussed the tests first reported in the Experentia article, stating that: "as expected, only the S-enantiomer had anti-inflammatory activity. The anti-inflammatory effects after administration of higher doses of R-flurbiprofen may be explained by an S-impurity of the administered R-enantiomer (purity: S-flurbiprofen, 98.5%; R-flurbiprofen, 99.1%) and/or by small amounts of S-flurbiprofen formed by inversion."

More recently, following the discovery of the differences between COX-1 and COX-2, some drug companies have set forth to make compounds which selectively inhibit COX-2, so as to achieve the desired anti-inflammatory and analgesic effects while avoiding the toxic effects associated with COX-1 inhibition. Some of these recent advances were discussed in a recent article in Science (Elizabeth Pennisi, "Building A Better Aspirin", Science 280:1191–92 (1988), and have even found their way to the mainstream media such as Jerome Groopman's article entitled "Superaspirin" (*The New Yorker* p.32–35 (1998)). These articles present the new COX-2 inhibitor drugs as far superior to the older NSAIDs and state that this new class of COX-2 inhibitors will eventually replace the older NSAIDs, which will "become dinosaurs." This current flurry of research and media activity makes it clear that a need remains for an anti-inflammatory compound characterized by an ability to selectively block prostaglandin production via the COX-2 pathway.

SUMMARY OF THE INVENTION

There is provided in accordance with one aspect of the present invention, a method of treating inflammation in an animal. The method comprises administering to the animal a dose of at least 2.5 milligrams of an enantiomerically pure R-NSAID per kilogram of said animal's body weight. In other embodiments, the administered dose is at least 5 mg/kg, at least 25 mg/kg, and at least 50 mg/kg of the animals body weight. In preferred embodiments of the methods, the R-NSAID is selected from the group consisting of R-ketoprofen, R-flurbiprofen, R-ketorolac, R-etodolac, R-tiaprofenic acid, R-suprofen, R-carprofen, R-pirprofen, and R-benoxaprofen. In an especially preferred embodiment, the R-NSAID is R-flurbiprofen.

In accordance with a further aspect of the present invention, there is provided a pharmaceutical composition for the treatment of inflammation. The pharmaceutical composition comes in a unit dosage form and comprises at least 200 milligrams of an enantiomerically pure R-NSAID. In other embodiments, the unit dosage form is at least 400 milligrams, at least 1,000 milligrams, and at least 3,500 milligrams. In preferred embodiments, the R-NSAID of the pharmaceutical composition is selected from the group consisting of R-ketoprofen, R-flurbiprofen, R-ketorolac, R-etodolac, R-tiaprofenic acid, R-suprofen, R-carprofen, R-pirprofen, and R-benoxaprofen. In an especially preferred embodiment, the R-NSAID is R-flurbiprofen.

DETAILED DESCRIPTION OF THE PREFERRED EMBODIMENTS

Although NSAIDs have been known for many years as anti-inflammatory drugs, the activity was believed to lie in the S-enantiomer only, due to its ability to inhibit the COX-2 enzyme. The R-enantiomer exhibits only minor inhibition of the COX-2 enzyme, and was thus believed to be inactive as an anti-inflammatory agent, though it was found to have utility for other indications.

It has surprisingly been found by the inventor herein that R-NSAIDs have anti-inflammatory activity when given at relatively high dosages, that is more than 2.5 mg/kg. The anti-inflammatory properties of R-NSAIDs is due to their ability to interfere with the biosynthesis of COX-2 by inhibiting COX-2 mRNA synthesis, rather than by just blocking the action of the enzyme itself. In order to effect the inhibition of COX-2 mRNA synthesis, the R-NSAID must be present at relatively high concentrations. Because the R-NSAID is selective in its action, that is it does not significantly inhibit either COX-1 mRNA synthesis or either of the COX enzymes themselves, it can be administered in the required high doses because the tissue protective effects of prostaglandins made through the COX-1 pathway are not interfered with.

Because of the unpleasant and undesirable side effects associated with the S-enantiomers, it is desired that the R-NSAIDs used in the pharmaceutical compositions and methods of the present invention be substantially free of the S-enantiomer, that is "enantiomerically pure." An enantiomerically pure R-NSAID, as that term is used herein, comprises preferably at least 98% R-NSAID, more preferably at least 99.5% R-NSAID, most preferably at least 99.9% R-NSAID.

For the methods and pharmaceutical compositions of the present invention, the enantiomerical purity is in reference to the R-NSAID as it exists prior to being administered to the animal host or patient. This is because both S- and R-arylpropionic acid NSAIDs are subject to interconversion by means of inversion when placed in vivo. The degree of inversion varies widely among the NSAIDs and is generally different for the R- and S-enantiomeric forms of a given compound. The degree of inversion for a given enantiomer may also vary by the dose given, the species of animal tested, the gender of animal tested, and the amount of time the enantiomer has been in the animal's system.

Preferred R-NSAIDs for use in the methods and pharmaceutical compositions of the present invention are those which are enantiomerically stable. As used herein, "enantiomerically stable" means that at a steady state, there is preferably no more than about 10% of the S-enantiomer of the NSAID in circulation, more preferably no more than 2%, most preferably no more. than about 1% of the S-enantiomer in circulation, the S-enantiomer having been formed in vivo from inversion of the R-enantiomer. Examples of enantiomerically stable R-NSAIDs are R-flurbiprofen (1.5% S-enantiomer in circulation at steady state in humans), R-ketoprofen (10% S), R-ketorolac (6% S), and R-etodolac (0% S).

A large number of R-NSAIDs which are preferred for use in the medicaments and methods of the present invention are commercially available. The enantiomeric purity of any given R-NSAID may vary among manufacturers. R-ketoprofen, R-flurbiprofen, and R-ketorolac are available through Sepracor, Inc. (Marlborough, Mass.); R-naproxen can be obtained as a sodium salt through Sigma Chemical Co.; R-etodolac is available from Wyeth-Ayerst, R-tiaprofenic acid is available through Roussel (France); R-suprofen is manufactured by McNiel Pharmaceuticals; R-carprofen is available from Roche (Switzerland); R-pirprofen is available through Carlo Elba (Italy); and R-benoxaprofen is manufactured by Eli Lilly and Co. (Indianapolis, Ind.). Additionally, racemates which can be resolved by methods known in the art, may be obtained from several of the above sources.

The most preferred R-NSAID for use in the methods and pharmaceutical compositions of the present invention is R-flurbiprofen, based on its superior enantiomeric stability in humans and availability in a very enantiomerically pure form, up to 99.97%.

This very pure form of R-flurbiprofen, was tested for anti-inflammatory activity by the carrageenan paw test. Seven groups of eight male Long Evans derived rats weighing 150±20 grams were fasted overnight. One hour after oral administration a suspension of the test substance in 2% Tween 80, as documented in Table 1 below, the right hind paw of each rat was injected intraplantarly with 0.1 ml of a 1% suspension of carrageenan. Three hours after injection, the hind paw volume was measured using a plethysmometer and recorded.

TABLE 1

RESULTS OF CARRAGEENAN PAW TEST

| Substance Tested | Dose | Result (Reduction of Edema) | Anti-Inflammatory Activity |
| --- | --- | --- | --- |
| Vehicle (2% Tween 80) | 10 ml/kg | 0% | No |
| Positive Control (Aspirin) | 150 mg/kg | 42% | Yes |
| R-Flurbiprofen | 40 mg/kg | 51% | Yes |
| R-Flurbiprofen | 20 mg/kg | 47% | Yes |
| R-Flurbiprofen | 10 mg/kg | 41% | Yes |
| R-Flurbiprofen | 5 mg/kg | 30% | Yes |

As seen in Table 1 above, R-flurbiprofen present at high doses exhibits anti-inflammatory action, that is it causes a statistically significant reduction of edema in the rat.

The pharmaceutical compositions of the present invention can be prepared in any desired form, for example, tablets, powders, capsules, sterile suspensions or solutions for parenteral administration, non-sterile suspensions or solutions for oral administration, suppositories, aerosols, and the like. Furthermore, the pharmaceutical compositions of the present invention may be administered by any route including oral, intravenous, intramuscular, vaginal, rectal, topical, transdermal, buccal, nasal, inhalation, and the like. The use of controlled release means and other drug delivery devices are contemplated by the inventor.

In addition to one or more R-NSAIDs, the pharmaceutical compositions of the present invention may optionally comprise carriers, fillers, diluents, granulating agents, lubricants, binders, disintegrating agents, release agents and the like. Preferred fillers include starch, glucose, lactose, mannitol, calcium phosphate, calcium carbonate, and cellulose. Preferred lubricants include talc, calcium stearate, and magnesium stearate. Preferred release agents include carboxymethyl cellulose, carboxymethyl starch, polyvinylpyrrolidone (PVP), and silica gel. Which optional ingredients are present and the quantity used is dependent upon many factors, including the form the medicament will take, the desired strength of the final composition, and the desired speed at which the active ingredients are to be released into the animal's system. It is within the abilities of one skilled in the art to create a suitable formulation for use in methods of the present invention, including the choice of optional ingredients and the amounts in which they are present.

The R-NSAIDs used in the methods and pharmaceutical compositions of the present invention may be present in the form of a pharmaceutically acceptable salt. When describing formulations used in the methods and compositions of the present invention, R-NSAID should be read as also including any of the pharmaceutically acceptable salts thereof. The term "pharmaceutically acceptable salt" as used herein refers to salts prepared from pharmaceutically acceptable, non-toxic acids or bases. Suitable pharmaceutically acceptable salts include inorganic salts, e.g. salts of aluminum, calcium, lithiun, magnesium, potassium, sodium and zinc, or organic salts, e.g. salts of lysine, N,N'-dibenzylethylenediamine, chloroprocaine, choline, diethanolamine, ethylenediamine, N-methylglucamine, procaine, and tris. A salt may be chosen to effect a particular rate of dissolution or uptake in the body, as is known in the art.

Of the available routes, the oral route is preferred, and oral solid preparations (e.g. tablets, capsules, caplets, powders, chewable tablets) are preferred over oral liquid preparations. The most preferred oral solid preparations are tablets. A common method of forming a suitable pressed tablet is to combine the powdered active material having a suitable particle size distribution with pharmaceutically compatible adjuvants, such as lubricants, inert diluents, dispersing agents, carriers binders, and the like, and then press the mixture in a suitable machine. Molded tablets may be made by molding the composition, which preferably comprises a mixture of powdered material comprising at least one R-NSAID and any optional adjuvants, moistened with an inert liquid diluent in a suitable molding machine as is known in the art. Molded tablets may also contain any optional material such as those described above. If the tablets are in chewable form, addition of one or more flavorings and sweeteners, such as saccharin, is preferred.

Another form for the oral route is the capsule. Capsules, preferably made of gelatin, may be filled with dry materials such as powder, granules and pellets or with a suspension such as that formed by mixing the R-NSAID with a material such as vegetable oil or other pharmaceutically compatible carrier.

Oral suspensions and solutions for use in the present invention preferably comprise at least one R-NSAID, water, sweetener (such as sugar, saccharin, or aspartame), a flavoring (such as mint, or any of the known FDA-approved artificial flavorings), and a suspension or emulsifying agent (such as Tween or tragacanth). Preferably such suspensions or solutions are made by first combining all ingredients other than the R-NSAID, and then mixing in a sufficient quantity of finely powdered R-NSAID to achieve a solution or suspension of desired strength.

Injectable solutions are preferably prepared by combining a salt of the R-NSAID with water or isotonic saline. Other materials such as preservatives, sugars, and other drugs may be added on an optional basis. After mixing, the solution is filtered and placed in a sterile container, such as a vial or plastic infusion bag. The concentration of the solution can vary widely, depending upon whether such solution is to be infused to a patient over time or administered via a single hypodermic injection.

The dose of R-NSAID may also take the form of a suppository for either rectal or vaginal administration. A suitable suppository composition comprises the active ingredient (R-NSAID) mixed with a carrier, such as a fat or polyglycol, having a melting point at or near body temperature. Alternatively, the carrier may be a material which dissolves when placed in the rectum or vagina. The suppository is preferably made by mixing powdered R-NSAID with the carrier, and then forming the mixture into a generally cylindrical or bullet shape of a size which allows for insertion.

Other dosage forms can be prepared by one skilled in the art by the use of known or later developed techniques which allow for the administration of a solid substance to an animal.

The quantity of R-NSAID used in the pharmaceutical compositions and methods of the present invention is dependent upon the body weight of the animal to whom the drug is administered and the frequency of dosing. It is preferred that the total daily dose for anti-inflammatory effect be at least 2.5 milligrams of R-NSAID per kilogram of body weight of the animal (2.5 mg/kg), preferably at least 5 mg/kg, more preferably 25–50 mg/kg or more. As the compounds and compositions of the present invention are not toxic, it is not foreseen that there is an upper limit to the dose at which the compounds of the present invention can be given. A dose comprising several grams of an R-NSAID is contemplated by the inventor.

The total quantity of dose may also be dependent upon the form which the dose takes and the relative efficiency or inefficiency of delivery of the drug by that particular dose form or route. For example, to achieve the same concentration of the drug in the body of the animal, it may be necessary to deliver a larger dose when a drug is administered via a relatively inefficient means such as a suppository or inhalation, as opposed to when the drug is administered by a more efficient method such as intravenous injection or orally.

The preferred total daily dose may be administered in a single dose or in smaller doses administered two, three, four, or more times during the day which, when summed together, equal the total daily dose. If a drug delivery device such as a transdermal patch is used, the dose may be administered continually over a period of hours. The determination as to whether and to what extent the total daily dose should be broken down into smaller doses administered throughout the day is dependent on several factors, including the half-life of the particular R-NSAID in the body, the speed at which the form of the R-NSAID becomes biologically available, and the total quantity of R-NSAID which needs to be administered.

Although the present invention has been described in terms of certain preferred embodiments, it is to be understood that the scope of the invention is not to be limited thereby. Instead, Applicant intends that the scope of the invention be limited solely by reference to the attached claims, and that variations on the formulation and dosages disclosed herein which are apparent to those of skill in the art will fall within the scope of Applicant's invention.

What is claimed is:

1. A method of treating inflammation in an animal, comprising administering to said animal a dose of at least 5 milligrams of an enantiomerically pure R-NSAID per kilogram of said animal's body weight.

2. The method of claim 1 wherein said dose is at least 25 milligrams of an enantiomerically pure R-NSAID per kilogram of said animal's body weight.

3. The method of claim 1 wherein said dose is at least 50 milligrams of an enantiomerically pure R-NSAID per kilogram of said animal's body weight.

4. The method of claim 1 wherein said R-NSAID is selected from the group consisting of R-ketoprofen, R-flurbiprofen, R-ketorolac, R-etodolac, R-tiaprofenic acid, R-suprofen, R-carprofen, R-pirprofen, and R-benoxaprofen.

5. The method of claim 1 wherein said R-NSAID is R-flurbiprofen.

* * * * *

UNITED STATES PATENT AND TRADEMARK OFFICE
CERTIFICATE OF CORRECTION

PATENT NO.    : 6,472,433 B2
DATED         : October 29, 2002
INVENTOR(S)   : William J. Wechter It is certified that error appears in the above-identified patent and that said Letters Patent is hereby corrected as shown below:

<u>Title page, Item [54] and Column 1, lines 1 and 2,</u>
Before "METHOD FOR TREATMENT OF INFLAMMATION WITH R-NSAIDS" please add -- PHARMACEUTICAL COMPOSITION AND --; and after text "OF INFLAMMATION" please delete "WITH R-NSAIDS".

Signed and Sealed this

Third Day of June, 2003

JAMES E. ROGAN
*Director of the United States Patent and Trademark Office*